United States Patent
McCullough

(10) Patent No.: US 9,724,495 B2
(45) Date of Patent: Aug. 8, 2017

(54) WEEPING BALLOON CATHETER WITH DRUG DELIVERY THROUGH DILATION BALLOON

(71) Applicant: Cook Medical Technologies LLC, Bloomington, IN (US)

(72) Inventor: Adam Brian McCullough, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 707 days.

(21) Appl. No.: 14/226,882

(22) Filed: Mar. 27, 2014

(65) Prior Publication Data

US 2014/0364834 A1      Dec. 11, 2014

Related U.S. Application Data

(60) Provisional application No. 61/833,125, filed on Jun. 10, 2013.

(51) Int. Cl.
*A61M 37/00* (2006.01)
*A61M 31/00* (2006.01)
*A61M 25/10* (2013.01)

(52) U.S. Cl.
CPC ....... *A61M 25/1011* (2013.01); *A61M 25/104* (2013.01); *A61M 25/10186* (2013.11); *A61M 2025/105* (2013.01); *A61M 2025/1013* (2013.01)

(58) Field of Classification Search
CPC .... A61M 2025/1013; A61M 2025/105; A61M 25/1002; A61M 25/1011; A61M 25/10186; A61M 25/1025; A61M 25/104

USPC ..................................................... 604/103.01
See application file for complete search history.

(56) References Cited

U.S. PATENT DOCUMENTS

| | | |
|---|---|---|
| 5,295,962 A | 3/1994 | Crocker et al. |
| 5,421,826 A | 6/1995 | Crocker et al. |
| 5,549,551 A | 8/1996 | Peacock, III et al. |
| 5,843,116 A | 12/1998 | Crocker et al. |
| 7,410,480 B2 * | 8/2008 | Muni ..................... A61B 5/411 604/509 |
| 8,034,022 B2 | 10/2011 | Boatman |
| 8,182,446 B2 | 5/2012 | Schaeffer et al. |
| 8,348,890 B2 * | 1/2013 | Gerrans ............. A61M 25/1011 604/101.02 |
| 2010/0249702 A1 | 9/2010 | Magana et al. |
| 2010/0305678 A1 * | 12/2010 | Alaswad ................. A61F 2/958 623/1.11 |
| 2012/0143054 A1 | 6/2012 | Eaton et al. |
| 2012/0310085 A1 | 12/2012 | Herweck et al. |

* cited by examiner

*Primary Examiner* — Jason Flick
(74) *Attorney, Agent, or Firm* — Liell & McNeil

(57) ABSTRACT

A weeping balloon catheter includes a catheter having an elongate tubular body defining a medical device lumen and a liquid delivery lumen. A dilation balloon is disposed at a distal end of the elongate tubular body and is in fluid communication with the liquid delivery lumen. The dilation balloon includes a fluid communication channel through an outer wall of the dilation balloon. A flow restriction member is positioned along the fluid communication channel and has an open position permitting fluid communication along the fluid communication channel and a closed position blocking fluid communication along the fluid communication channel. A drug delivery path of the weeping balloon catheter is defined by the liquid delivery lumen and the dilation balloon.

19 Claims, 3 Drawing Sheets

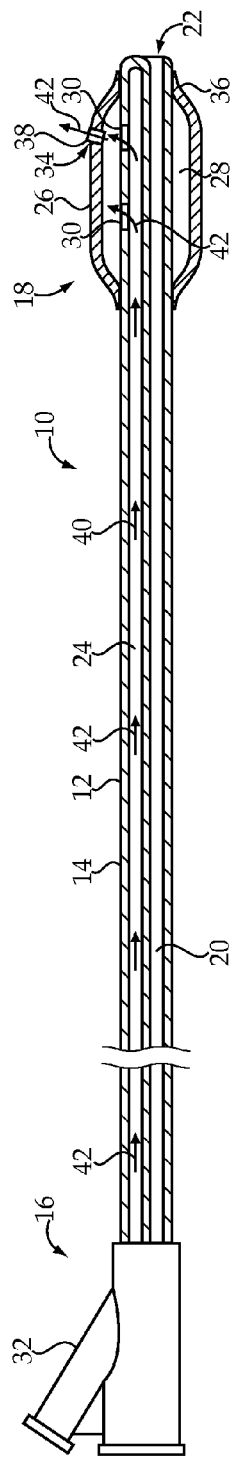
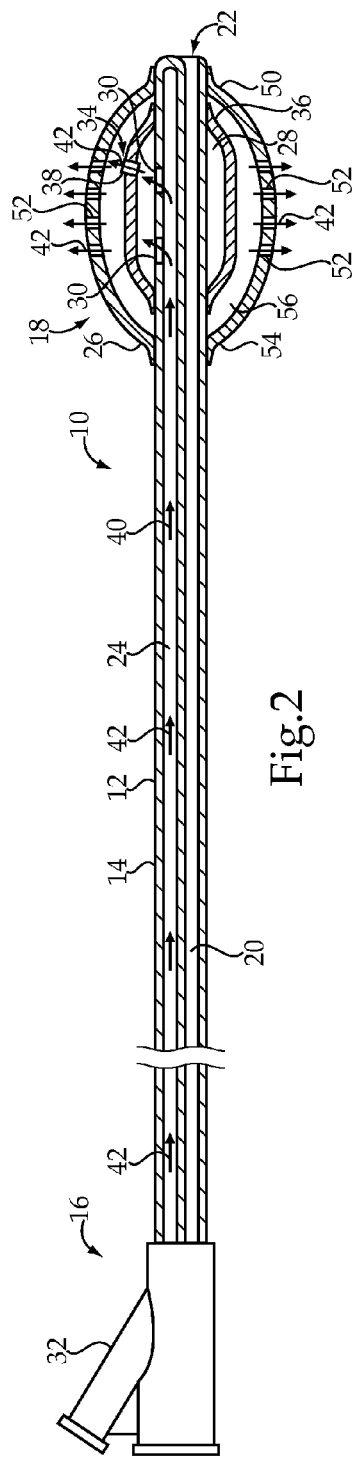
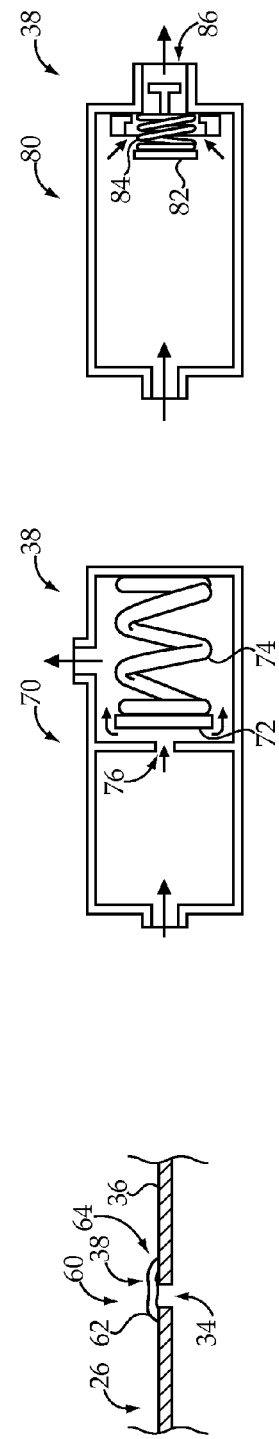
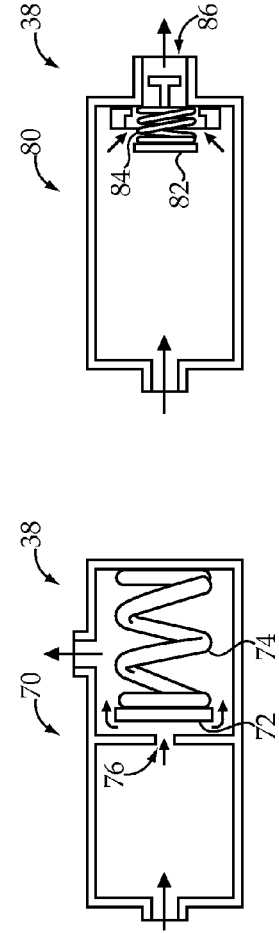

WEEPING BALLOON CATHETER WITH DRUG DELIVERY THROUGH DILATION BALLOON

TECHNICAL FIELD

The present disclosure relates generally to a weeping balloon catheter and more particularly to a weeping balloon catheter having a drug delivery path defined by a liquid delivery lumen and a dilation balloon.

BACKGROUND

Catheters provide minimally invasive means for treating various conditions. For example, angioplasty is a common procedure used to treat cardiovascular disease. During an angioplasty procedure, a medical device, such as a balloon catheter, may be percutaneously inserted into a vessel narrowed by stenosis. The balloon may be expanded at the stenosis to ultimately restore blood flow through the vessel. In some cases, a stent may be placed at the narrowed portion of the vessel to help keep the vessel open. In either case, it may be desirable to combine the balloon and/or stent treatment with the application of therapeutic drugs. In particular, it may be desirable to deliver a therapeutic drug exclusively to the narrowed portion of the vessel. In some cases, a therapeutic drug may be used to reduce restenosis at the treatment site.

A number of catheter devices have been developed to administer a therapeutic agent locally to tissue while dilating a body vessel, such as during delivery of a therapeutic agent to a dilated portion of a coronary artery in an angioplasty procedure. For instance, U.S. Pat. No. 8,182,446 to Schaeffer et al. discloses a catheter having a dual balloon assembly. The dual balloon assembly includes an inner balloon and a porous outer balloon concentrically arrayed around the inner balloon. Radial outward expansion of the inner balloon may urge the outer balloon into contact with the wall of a vessel, where a therapeutic agent may be delivered from the catheter through apertures in the outer balloon. Such a balloon catheter device is also referred to as a weeping balloon. Weeping balloons typically require a profile size sufficient to accommodate a wire guide lumen, an inflation lumen, and a drug delivery lumen. Although weeping balloons have definite advantages, it should be appreciated that there is a continuing need for improved catheter devices.

The present disclosure is directed toward one or more of the problems or issues set forth above.

SUMMARY OF THE DISCLOSURE

In one aspect, a weeping balloon catheter includes a catheter having an elongate tubular body defining a medical device lumen and a liquid delivery lumen. A dilation balloon is disposed at a distal end of the elongate tubular body and is in fluid communication with the liquid delivery lumen. The dilation balloon includes a fluid communication channel through an outer wall of the dilation balloon. A flow restriction member is positioned along the fluid communication channel and has an open position permitting fluid communication along the fluid communication channel and a closed position blocking fluid communication along the fluid communication channel. A drug delivery path of the weeping balloon catheter is defined by the liquid delivery lumen and the dilation balloon.

In another aspect, a method of operating a weeping balloon catheter is provided. The weeping balloon catheter includes a catheter having an elongate tubular body defining a medical device lumen and a liquid delivery lumen and a dilation balloon disposed at a distal end of the elongate tubular body. The dilation balloon is in fluid communication with the liquid delivery lumen and includes a fluid communication channel through an outer wall of the dilation balloon. A flow restriction member is positioned along the fluid communication channel and has an open position permitting fluid communication along the fluid communication channel and a closed position blocking fluid communication along the fluid communication channel. The method includes steps of advancing the distal end of the weeping balloon catheter toward a target site within a body lumen, and advancing a therapeutic agent through the liquid delivery lumen and into the dilation balloon. The method also includes a step of inflating the dilation balloon using the therapeutic agent while the flow restriction member is in the closed position.

BRIEF DESCRIPTION OF THE DRAWINGS

FIG. 1 is a partially sectioned side diagrammatic view of a weeping balloon catheter having a dilation balloon, according to one embodiment of the present disclosure;

FIG. 2 is a partially sectioned side diagrammatic view of a weeping balloon catheter having a dilation balloon and a drug delivery balloon, according to another embodiment of the present disclosure;

FIG. 3 is a partially sectioned side diagrammatic view of a flow restriction member in the form of a check valve that may be positioned along a fluid communication channel of the weeping balloon catheter of FIG. 1 or FIG. 2;

FIG. 4 is a partially sectioned side diagrammatic view of a flow restriction member in the form of a pressure actuated valve that may be positioned along a fluid communication channel of the balloon catheter of FIG. 1 or FIG. 2;

FIG. 5 is a partially sectioned side diagrammatic view of a flow restriction member in the form of a flow actuated valve that may be positioned along a fluid communication channel of the balloon catheter of FIG. 1 or FIG. 2;

DETAILED DESCRIPTION

Figure 6:
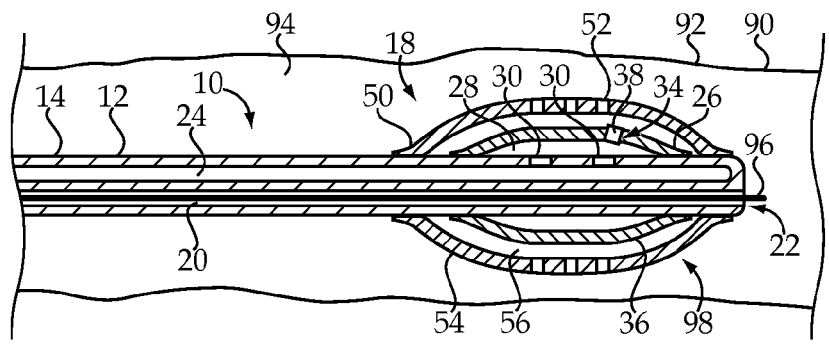
FIG. 6 is a partially sectioned side diagrammatic view of a vascular structure of a patient depicting one stage of a treatment procedure using the weeping balloon catheter of FIG. 1.

Referring to FIG. 1, there is shown a weeping balloon catheter 10 according to one embodiment of the present disclosure. The weeping balloon catheter 10 generally includes a catheter 12 having an elongate tubular body 14 having a proximal end 16 and a distal end 18. The elongate tubular body 14 may be made from any common medical tube material, such as, for example, polytetrafluoroethylene (PTFE), high density polyethylene (HDPE), nylon, polyetheretherketone (PEEK), or any vinyl, plastic, rubber, or silicone, and may exhibit both stiffness, or firmness, and flexibility. Materials as well as dimensions may vary depending on the particular application. In the present disclosure, "proximal" will be used to refer to the end of a component or feature that is closest to a clinician, while "distal" is used to refer to a component or feature that is farthest away from the clinician. Such meanings are consistent with conventional use of the terms and, as such, should be understood by those skilled in the art.

The elongate tubular body 14 defines a medical device lumen 20 extending from the proximal end 16 to an opening 22 through the distal end 18. Although the medical device lumen 20 may have various uses, according to one example, the medical device lumen 20 may be used for advancing the catheter 12 over a wire guide (not shown) during a treatment procedure. The elongate tubular body 14 also defines a liquid delivery lumen 24 extending from the proximal end 16 to a dilation balloon 26 disposed, or mounted, at the distal end 18 of the elongate tubular body 14. The liquid delivery lumen 24 may be in fluid communication with an interior space 28 of the dilation balloon 26 via openings 30 through the elongate tubular body 14. A proximal fitting 32 may provide an interface for communicating with one or both of the medical device lumen 20 and the liquid delivery lumen 24, in a manner known to those skilled in the art.

The dilation balloon 26 includes a fluid communication channel 34 through an outer wall 36 of the dilation balloon 26. The fluid communication channel 34 may be an opening sized for receiving a flow restriction member 38. In particular, the flow restriction member 38 may be positioned along the fluid communication channel 34 and has an open position permitting fluid communication along the fluid communication channel 34 and a closed position blocking fluid communication along the fluid communication channel 34. Various embodiments of the flow restriction member 38 are presented below.

When the flow restriction member 38 is in the closed position, the dilation balloon 26 may be inflated, or expanded, by passing a fluid through the liquid delivery lumen 24, into the dilation balloon 26 through the openings 30, and blocking fluid along the fluid communication channel 34 using the closed position of the flow restriction member 38. In the open position, however, fluid is released from the dilation balloon 26 through the flow restriction member 38 of the fluid communication channel 34. If a liquid, such as a therapeutic agent, is advanced through the liquid delivery lumen 24, a drug delivery path 40, as shown using arrows 42, is defined by the liquid delivery lumen 24 and the dilation balloon 26.

Turning now to FIG. 2, and according to some embodiments, a drug delivery balloon 50 may be disposed at least partially over the dilation balloon 26 and may include at least one drug release opening 52 through an outer wall 54 of the drug delivery balloon 50. However, it should be appreciated that the drug delivery balloon 50 may not be required. According to some embodiments, an array of drug release openings 52 may be provided. The drug delivery balloon 50 is preferably positioned such that an interior 56 of the drug delivery balloon 50 is in fluid communication with the dilation balloon 26 along the fluid communication channel 34. In particular, the drug delivery balloon 50 may receive a fluid, such as a liquid, from the dilation balloon 26 when the flow restriction member 38 of the fluid communication channel 34 is in the open position. The closed position of the flow restriction member 38, as mentioned above, may restrict fluid, such as a liquid, from advancing from the dilation balloon 26 to the drug delivery balloon 50 via the fluid communication channel 34. According to the embodiment of FIG. 2, the drug delivery path 40 may be defined sequentially by the liquid delivery lumen 24, the dilation balloon 26, and the drug delivery balloon 50.

Although the flow restriction member 38 may include any of a variety of forms and/or configurations, some examples are provided herein. According to some embodiments, the flow restriction member 38 may be a valve biased to the closed position. For example, as shown in FIG. 3, the flow restriction member 38 may be a check valve 60, embodied most simply as a flap 62 having a hinged connection 64 to the dilation balloon 26 positioned over the fluid communication channel 34 and being biased to the closed position. As should be appreciated, the flap 62 may be urged from the closed position to the open position using fluid flow introduced into the dilation balloon 26.

Alternatively, as shown in FIG. 4, the flow restriction member 38 may be a pressure actuated valve 70 having a threshold opening pressure at which the pressure actuated valve 70 transitions from the closed position to the open position. For example, the pressure actuated valve 70 may include a valve member, such as a gasket, 72 that is biased to a closed position by a spring member 74. According to the closed position, the gasket 72 is urged by the spring member 74 to cover, or block fluid flow through, a pressure communication port 76. The cross sectional area of the pressure communication port 76, the cross sectional area of the gasket 72, and the force provided by the spring member 74 may all be selected to provide a desired threshold opening pressure. These values may also be selected to provide a desired threshold closing pressure at which the pressure actuated valve 70 returns to the closed position. According to some embodiments, the threshold opening pressure is at least double the threshold closing pressure. It should be appreciated that, according to this embodiment and others, the spring member 74 may be any component or structure providing spring-like characteristics and should not be limited to any particular spring embodiment. The same goes for other exemplary components described herein.

Yet alternatively, the flow restriction member 38 may be a valve biased to the open position. For example, as shown in FIG. 5, the flow restriction member 38 may be a flow actuated valve 80 having a threshold at which the flow actuated valve 80 transitions from the open position to the closed position. Referring to FIG. 5, increased liquid flow may move a plunger 82 against the bias of a spring member 84 to cover, or block fluid flow through, an opening 86. Reducing pressure or flow may permit the plunger 82 to return to the biased closed position. The spring force and flow restriction may be selected to provide a desired flow opening and closing characteristics.

INDUSTRIAL APPLICABILITY

Turning now to FIG. 6, a percutaneous vascular procedure using the weeping balloon catheter 10, according to the embodiment of FIG. 2, will be discussed with reference to a vascular structure 90 of a patient. Although a vascular structure 90 is shown, the present disclosure may be applicable to alternative bodily structures and lumens. The vascular structure 90, as should be appreciated, may include a vessel wall 92 defining a lumen 94. Although not shown, it should be appreciated that a clinician may first use an introducer to gain access to the vascular structure 90 in a known manner. Next, as shown in FIG. 6, the catheter 12 may be inserted through the introducer, over a standard wire guide 96, and into the vascular structure 90. The catheter 12 may be advanced such that the distal end 18 of the catheter 12 and, more particularly, the dilation balloon 26 and the drug delivery balloon 50 are positioned at a target site 98. Although not shown or discussed in great detail, the target site 98 may be a narrowed portion of the vascular structure 90.

Figure 7:
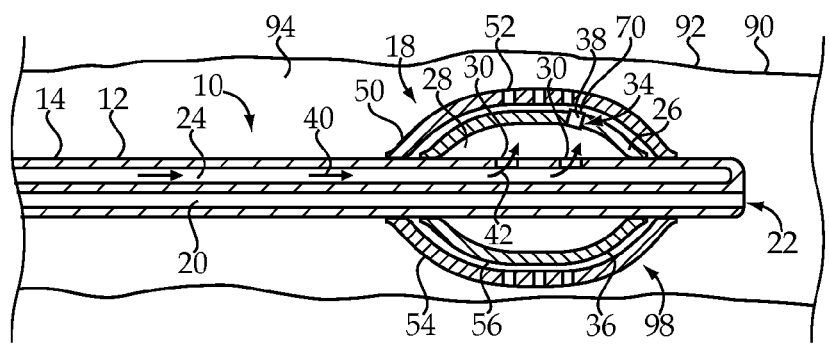
FIG. 7 is a partially sectioned side diagrammatic view of the vascular structure at another procedure stage, according to an embodiment using a pressure actuated valve.

The standard wire guide 96 may be removed and, at a next stage of the procedure shown in FIG. 7, a therapeutic agent may be advanced through the liquid delivery lumen 24 and into the dilation balloon 26. Although the drawings reflect removal of the wire guide 96, it should be appreciated that the wire guide 96 may remain in place throughout the procedure. According to embodiments utilizing a flow restriction member 38 biased to the closed position, such as, for example, the pressure actuated valve 70 of FIG. 4, the dilation balloon 26 may be inflated using the therapeutic agent while the flow restriction member 38 is in the closed position. In particular, the therapeutic agent may be advanced at a nominal pressure, while the pressure actuated valve 70 blocks advancement of the therapeutic agent along the fluid communication channel 34. As a result, the dilation balloon 26 is inflated to an expanded position using the therapeutic agent.

Figure 8:
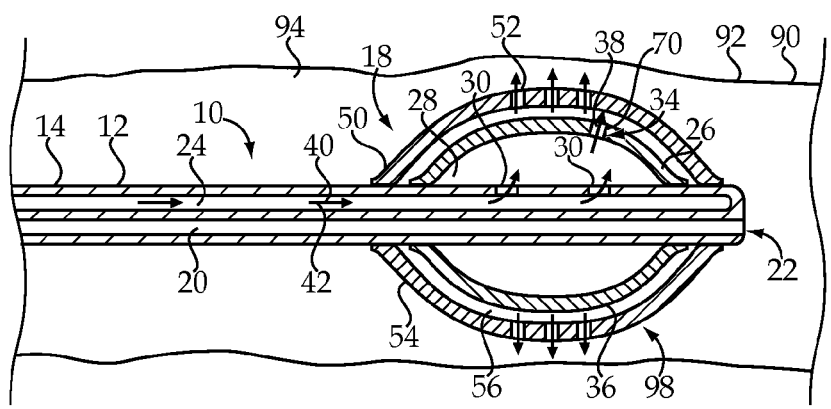
FIG. 8 is a partially sectioned side diagrammatic view of the vascular structure at another procedure stage utilizing the pressure actuated valve embodiment.

Next, as shown in FIG. 8, a pressure of the therapeutic agent may be increased from the nominal pressure to an increased pressure that is greater than the threshold opening pressure of the pressure actuated valve 70. As a result, the pressure actuated valve 70 may be transitioned from the biased closed position to an actuated open position responsive to the increased pressure. With the pressure actuated valve 70 in the open position, the therapeutic agent may advance along the fluid communication channel 34, pass into the drug delivery balloon 50, and be released from the drug delivery balloon 50 through drug release openings 52 with the dilation balloon 26 in the expanded position.

The pressure of the therapeutic agent may be decreased from the increased pressure to a decreased pressure that is less than the threshold closing pressure of the pressure actuated valve 70 after releasing the therapeutic agent from the drug delivery balloon 50. As a result, the pressure actuated valve 70 may be transitioned from the actuated open position to the biased closed position responsive to the decreased pressure. As stated above, and according to some embodiments, the threshold closing pressure may be less than half the threshold opening pressure. However, it should be noted that the operational characteristics of the selected flow restriction member 38 may be selected based on a desired performance with respect to the particular procedure being performed.

Figure 9:
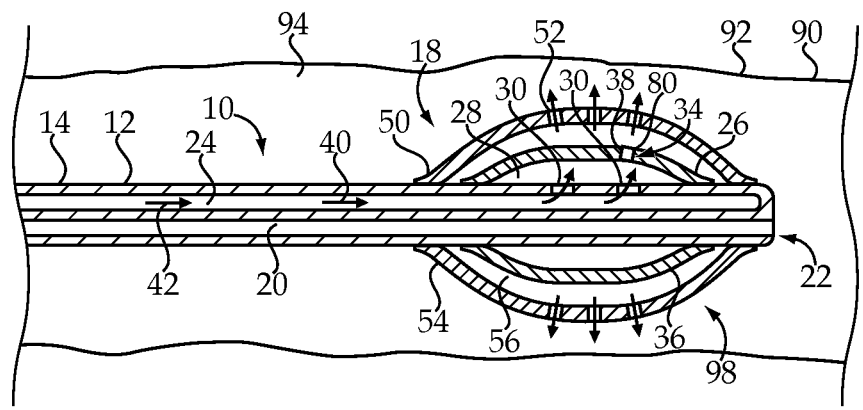
FIG. 9 is a partially sectioned side diagrammatic view of the vascular structure at a procedure stage, according to an embodiment using a flow actuated valve.
Figure 10:
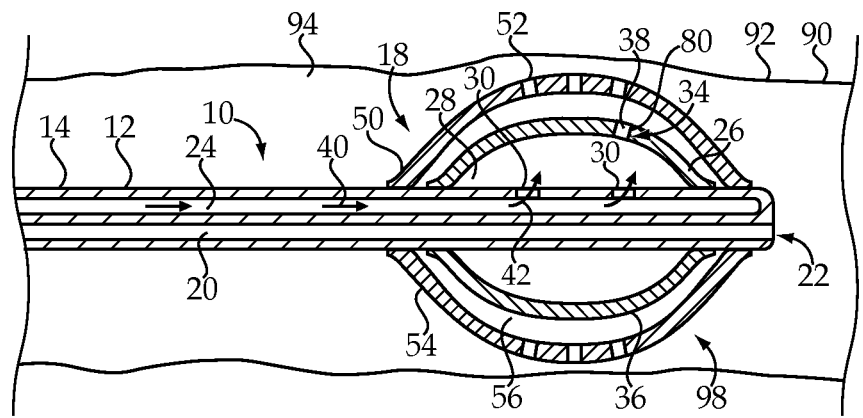
FIG. 10 is a partially sectioned side diagrammatic view of the vascular structure at another procedure stage utilizing the flow actuated valve.

Turning now to FIG. 9, and according to embodiments utilizing a flow restriction member 38 biased to the open position, such as, for example, the flow actuated valve 80 of FIG. 5, the therapeutic agent may be advanced at a nominal pressure along the drug delivery lumen 24, into the dilation balloon 26, and through the flow actuated valve 80. The therapeutic agent is then passed into the drug delivery balloon 50 and released from the drug delivery balloon 50 through the drug release openings 52. As should be appreciated, the therapeutic agent, according to this embodiment, may be released from the drug delivery balloon 50 with the dilation balloon 26 in a non-expanded position.

The flow of the therapeutic agent may be increased to exceed the threshold of the flow actuated valve 80. The flow actuated valve 80 may then transition from the biased open position to the actuated closed position in response to the increase in flow. As a result, advancement of the therapeutic agent along the fluid communication channel 34 is blocked using the actuated closed position of the flow actuated valve 80, and the dilation balloon 26 is inflated to an expanded position. Thus, according to this embodiment, the dilation balloon 26 may be inflated after the therapeutic agent is released from the drug delivery balloon 50. According to some embodiments, a portion or even a majority of the therapeutic agent may remain in the drug delivery balloon 50, which may result in an expanded state of the drug delivery balloon 50, and may be released responsive to the expansion of the dilation balloon 26.

The weeping balloon catheter of the present disclosure permits a lower profile than conventional weeping balloon catheters. In particular, the disclosed weeping balloon catheter utilizes a common lumen for inflating the dilation balloon and releasing a therapeutic agent through the drug delivery balloon. The therapeutic agent may be used to expand the dilation balloon and actuate a flow restriction member positioned along a fluid communication channel that fluidly connects the dilation balloon and the drug delivery balloon. Characteristics of the flow restriction member may be varied to produce desired effects during treatment. For example, the therapeutic agent may be released at various stages of expansion of the dilation balloon.

It should be understood that the above description is intended for illustrative purposes only, and is not intended to limit the scope of the present disclosure in any way. Thus, those skilled in the art will appreciate that other aspects of the disclosure can be obtained from a study of the drawings, the disclosure and the appended claims.

What is claimed is:

1. A weeping balloon catheter, comprising:
   a catheter having an elongate tubular body defining a medical device lumen and a liquid delivery lumen;
   a dilation balloon disposed at a distal end of the elongate tubular body and in fluid communication with the liquid delivery lumen, wherein the dilation balloon includes a fluid communication channel through an outer wall of the dilation balloon; and
   a flow restriction member positioned along the fluid communication channel and having an open position permitting fluid communication along the fluid communication channel and a closed position blocking fluid communication along the fluid communication channel;
   wherein a drug delivery path of the weeping balloon catheter is defined by the liquid delivery lumen and the dilation balloon.

2. The weeping balloon catheter of claim 1, further including:
   a drug delivery balloon disposed at least partially over the dilation balloon and including at least one drug release opening through an outer wall of the drug delivery balloon, wherein the drug delivery balloon is in fluid communication with the dilation balloon along the fluid communication channel;
   wherein the drug delivery path is defined sequentially by the liquid delivery lumen, the dilation balloon, and the drug delivery balloon.

3. The weeping balloon catheter of claim 2, wherein the flow restriction member is a valve biased to the closed position.

4. The weeping balloon catheter of claim 3, wherein the valve is a check valve.

5. The weeping balloon catheter of claim 3, wherein the valve is a pressure actuated valve having a threshold opening pressure at which the pressure actuated valve transitions from the closed position to the open position.

6. The weeping balloon catheter of claim 5, wherein the pressure actuated valve has a threshold closing pressure at which the pressure actuated valve returns to the closed position, wherein the threshold opening pressure is at least double the threshold closing pressure.

7. The weeping balloon catheter of claim 2, wherein the flow restriction member is a valve biased to the open position.

8. The weeping balloon catheter of claim 7, wherein the valve is a flow actuated valve having a threshold at which the flow actuated valve transitions from the open position to the closed position.

9. The weeping balloon catheter of claim 1, wherein the elongate tubular body defines exactly two lumens including the medical device lumen and the liquid delivery lumen.

10. A method of operating a weeping balloon catheter, the weeping balloon catheter including a catheter having an elongate tubular body defining a medical device lumen and a liquid delivery lumen, a dilation balloon disposed at a distal end of the elongate tubular body and in fluid communication with the liquid delivery lumen, wherein the dilation balloon includes a fluid communication channel through an outer wall of the dilation balloon, and a flow restriction member positioned along the fluid communication channel and having an open position permitting fluid communication along the fluid communication channel and a closed position blocking fluid communication along the fluid communication channel, and wherein a drug delivery path of the weeping balloon catheter is defined the liquid delivery lumen and the dilation balloon, the method comprising steps of:
advancing the distal end of the weeping balloon catheter toward a target site within a body lumen;
advancing a therapeutic agent through the liquid delivery lumen and into the dilation balloon; and
inflating the dilation balloon using the therapeutic agent while the flow restriction member is in the closed position.

11. The method of claim 10, further including releasing the therapeutic agent from the dilation balloon while the flow restriction member is in the open position.

12. The method of claim 10, further including advancing the therapeutic agent sequentially through the liquid delivery lumen, the dilation balloon, the fluid communication channel, and a drug delivery balloon disposed at least partially over the dilation balloon.

13. The method of claim 12, further including releasing the therapeutic agent from the drug delivery balloon through at least one drug release opening through an outer wall of the drug delivery balloon.

14. The method of claim 12, further including:
advancing the therapeutic agent at a nominal pressure;
blocking advancement of the therapeutic agent along the fluid communication channel using a pressure actuated valve having a biased closed position and a threshold opening pressure; and
inflating the dilation balloon to an expanded position responsive to the nominal pressure and the biased closed position.

15. The method of claim 14, further including:
increasing a pressure of the therapeutic agent from the nominal pressure to an increased pressure that is greater than the threshold opening pressure;
transitioning the pressure actuated valve from the biased closed position to an actuated open position responsive to the increased pressure; and
releasing the therapeutic agent from the drug delivery balloon with the dilation balloon in the expanded position.

16. The method of claim 15, further including:
decreasing the pressure of the therapeutic agent from the increased pressure to a decreased pressure that is less than a threshold closing pressure of the pressure actuated valve after releasing the therapeutic agent from the drug delivery balloon; and
transitioning the pressure actuated valve from the actuated open position to the biased closed position responsive to the decreased pressure.

17. The method of claim 16, wherein the threshold closing pressure is less than half the threshold opening pressure.

18. The method of claim 12, further including:
advancing the therapeutic agent at a nominal pressure through a flow actuated valve positioned along the fluid communication channel and having a biased open position and a threshold at which the flow actuated valve transitions from the biased open position to an actuated closed position; and
releasing the therapeutic agent from the drug delivery balloon with the dilation balloon in a non-expanded position.

19. The method of claim 18, further including:
increasing a flow of the therapeutic agent to exceed the threshold;
transitioning the flow actuated valve from the biased open position to the actuated closed position in response to increasing the flow;
blocking advancement of the therapeutic agent along the fluid communication channel using the actuated closed position of the flow actuated valve; and
inflating the dilation balloon to an expanded position after the therapeutic agent is released from the drug delivery balloon in response to the actuated closed position.

* * * * *